United States Patent [19]

Warriner

[11] Patent Number: Plant 5,645

[45] Date of Patent: Jan. 28, 1986

[54] ROSE PLANT JACPO

[75] Inventor: William A. Warriner, Tustin, Calif.

[73] Assignee: Jackson & Perkins Company, Medford, Oreg.

[21] Appl. No.: 631,564

[22] Filed: Jul. 16, 1984

[51] Int. Cl.[4] ..... A01H 5/00

[52] U.S. Cl. ..... Plt./8

[58] Field of Search ..... Plt./8

*Primary Examiner*—Robert E. Bagwill

*Attorney, Agent, or Firm*—Manford R. Haxton

[57] ABSTRACT

A miniature rose variety characterized by the unique combination of its high production of light yellow buds on 12" to 14" stems, many of which are borne in clusters; its resistance to rose powdery mildew; its lack of fragrance.

1 Drawing Figure

This present invention relates to a new and distinct variety of rose plant of the miniature class which was originated by crossing the variety Rise 'n Shine, U.S. Plant Pat. No. 4,231, with an unnamed variety.

The primary objective of this breeding was to produce a new rose variety of the miniature class able to produce vigorous, dense growth, and an abundance of long-pointed yellow buds on stems suitable for cut flower use. This objective was substantially achieved along with other desirable improvements as evidenced by the following unique combination of characteristics which are outstanding in the new variety and which distinguish it from its parents as well as from all other varieties of which I am aware:

1. Vigorous miniature plant up to 24" in height outside, approximately 48" to 60" in greenhouse;
2. Cutting stems mostly 12" to 14" in length;
3. Frequent production of clusters of 4 to 6 buds;
4. Light yellow buds and open blooms;
5. Strong resistance to rose powdery mildew;
6 Relatively long, but few prickles.

Asexual reproduction of this new variety by budding, as performed at Wasco, Calif., shows that the foregoing characteristics and distinctions come true to form and are established and transmitted through succeeding propagations.

The accompanying illustration shows typical specimens of the vegetative growth and flowers of this new variety in different stages of development, depicted in color as nearly true as it is reasonably possible to make the same in a color illustration of this character.

The following is a detailed description of my new rose cultivar with color in terminology in accordance with The Royal Horticultural Society Colour Chart except where ordinary dictionary significance of color is indicated:

Parentage:
- *Seed parent.*—Rise 'n Shine.
- *Pollen parent.*—Unnamed variety.

Classification:
- *Botanical.*—Rosa hybrid.
- *Commercial.*—Miniature.

FLOWER

Observations made from specimens grown in a greenhouse at Irvine, Calif. in June.

Blooming habit: Continuous.

Bud:
- *Size.*—$\frac{3}{4}$" to 1".
- *Form.*—Long.
- *Color.*—When sepals first divide, Yellow Orange 15B; when half blown, upper side of petals Yellow Orange 15C, often fading to near white on distal portion of petals: lower side of petals Yellow Orange 15C.
- *Sepals.*—Color: Green 138B. Three appendaged sepals lightly appendaged. Two unappendaged sepals hairy edged.
- *Receptacle.*—Color: Green 138B. Shape: Funnel. Size: Large, broad. Surface: Lightly pubescent.
- *Peduncle.*—Length: Short. Surface: Prickly and pubescent. Color: Light green. Strength: Stiff, erect, slender.
- *Opening.*—Spirally unfolding.

Open bloom:
- *Size.*—Small. Average Open size 2"–$2\frac{1}{2}$".
- *Borne.*—Single, or several together.
- *Stems.*—Medium, strong.
- *Form.*—When first open, high center. Permanence: Flattens; all petals curl, quill fashion.
- *Petalage.*—Number of petals under normal conditions: 25–30.
- *Color.*—Center of flower: Upper side of petals, Yellow Orange 15B, occasionally lighter 15D to near white; reverse side of petals, yellow orange 15B. Base of petals, Yellow Orange 15B. Major color: Yellow Orange 15B to near white on some flowers.
- *Variegations.*—None.
- *Discoloration.*—General tonality at end of first day: Yellow Orange 15C. Third day: Yellow Orange 15C.
- *Fragrance.*—None.

Petals:
- *Texture.*—Thin.
- *Shape.*—Round.
- *Form.*—Edges slightly quilled.
- *Arrangement.*—Imbricated. Petaloids in center, few.
- *Persistence.*—Drop off cleanly.
- *Lastingness.*—On the plant, long. As cut flower, long.

Reproductive parts:
- *Anthers.*—Relatively large. Color: Yellow. Arrangement: Regular around styles.
- *Filaments.*—Color: Yellow.

*Pollen.*—Gold yellow.
*Styles.*—Color: Red — Purple 61A.
*Stigmas.*—Color: Greenish white.

PLANT

Form: Bush.
Growth: Very vigorous; producing mostly 12" to 14" stems when grown in a greenhouse for cut flowers.
Foliage: Number of leaflets on normal mid-stem leaves: 5 or 7.
*Size.*—Small.
*Quantity.*—Normal.
*Color.*—New foliage: Greyed Purple 187A. Old foliage: Normal green.
Leaflets:
*Shape.*—Elliptic.
*Texture.*—Leathery.
*Edge.*—Serrated.
*Serration.*—Single, small.
*Petiole.*—Rachis: Color: Reddish. Underside: With prickles.
*Stipules.*—Long, edges glandular.

*Disease resistance.*—Resistant to mildew under normal growing conditions at Irvine, Calif.
Wood:
*New wood.*—Color: Reddish. Bark: Smooth.
*Old wood.*—Color: Green. Bark: Smooth.
Prickles:
*Quantity.*—On main canes from base: Ordinary. On laterals from main canes: Ordinary.
*Form.*—Very long, hooked slightly downward.
*Color when young.*—Red.
Small prickles:
*Quantity.*—On main stalks, none. On laterals, none.

I claim:

1. A new and distinct variety of rose plant of the miniature class, substantially as herein shown and described, characterized particularly as to novelty by the unique combination of its high production of light yellow buds on 12" to 14" stems, many of which are borne in clusters; its resistance to rose powdery mildew; its lack of fragrance.

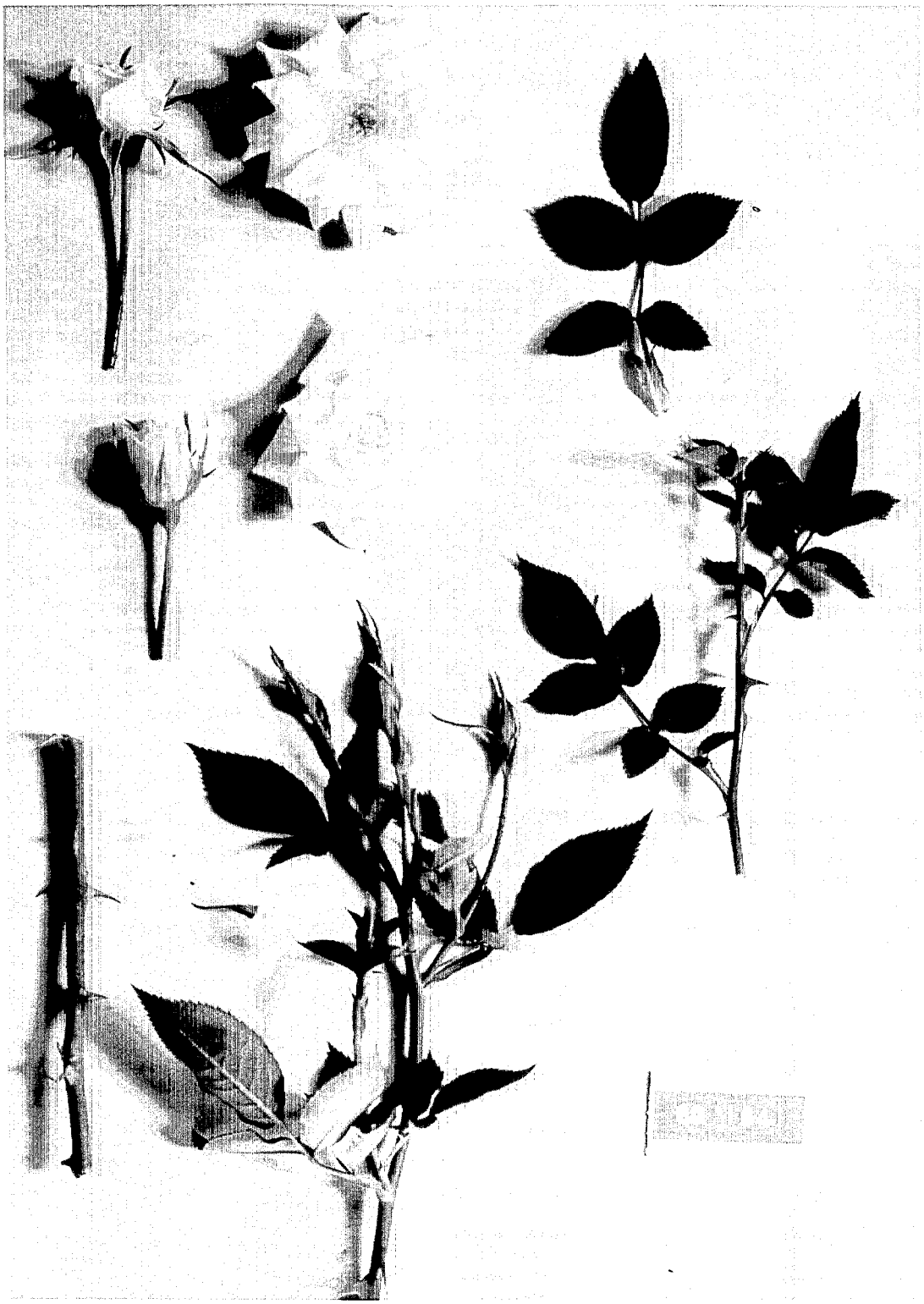

* * * * *